United States Patent [19]

Aronson et al.

[11] 4,346,073
[45] Aug. 24, 1982

[54] HEPATITIS B IMMUNE GLOBULIN USED TO INACTIVATE HEPATITIS B VIRUS IN INJECTABLE BIOLOGICAL PRODUCTS

[75] Inventors: David L. Aronson; Edward Tabor; Robert J. Gerety, all of Bethesda, Md.

[73] Assignee: The United States of America as represented by the Department of Health and Human Services, Washington, D.C.

[21] Appl. No.: 139,236

[22] Filed: Apr. 11, 1980

[51] Int. Cl.$^3$ ............................................. A61K 39/42
[52] U.S. Cl. ........................................ 424/86; 424/85; 260/112 B
[58] Field of Search ....................... 424/85, 86, 88, 89; 260/112 B

[56] References Cited

U.S. PATENT DOCUMENTS 4,021,540  5/1977  Pollack et al. ........................ 424/86
4,087,519  5/1978  Trepo .................................... 424/86
4,174,388  11/1979  McAleer et al. ..................... 424/86

OTHER PUBLICATIONS

Tabor et al., "A New Use for High Titer Immunoglobulin for the Prevention of Hepatitis B", Hepatitis Scientific Memoranda, Nov. 1979.
Tabor et al., "A New Use for High Titer Immunoglobulin, for the Prevention of Hepatitis B", Proceeding of Immunology Workshop, Oct. 1979.

*Primary Examiner*—Blondel Hazel
*Attorney, Agent, or Firm*—John S. Roberts, Jr.

[57] ABSTRACT

The utilization of hepatitis B immune globulin as a preparation for preventing transmission of the hepatitis B virus (HBV) by injectable biologics, by incubation of the injectable biologics and hepatitis B immune globulin together in vitro prior to administration to patient. The hepatitis B immune globulin is utilized in a dosage of 5 ml and in a preferred titer of 1 to 100,000. The titer may vary to a range of 1 to 100 concentration with an intermediate range of 1 to 1,000 ranging down to 1 to 100,000. Also there may be used other immune globulins such as immune serum globulin (ISG).

5 Claims, No Drawings

HEPATITIS B IMMUNE GLOBULIN USED TO INACTIVATE HEPATITIS B VIRUS IN INJECTABLE BIOLOGICAL PRODUCTS

The present invention relates to the utilization of hepatitis B immune globulin as a preparation for preventing transmission of the hepatitis B virus (HBV) by injectable biologic products, by incubation of the product and hepatitis B immune globulin together in vitro prior to administration to patient. The hepatitis B immune globulin is utilized in a dosage of 5 ml. The administration of the hepatitis B immume globulin has been utilized in cases of laboratory animals as well as humans. Other immune globulins such as immune serum globulin (ISG) may also be used.

The 5 ml dosage of hepatitis B immune globulin is utilized in a preferred titer of 1 to 100,000. The titer may vary to a range of 1 to 100 concentration with an intermediate range of 1 to 1,000 ranging down to 1 to 100,000.

Hepatitis B immune globulin, a preparation derived from the plasma of persons with high titers of antibody to hepatitis B surface antigen, has been licensed by the Food and Drug Administration for administration to persons following exposure to small doses of hepatitis B virus.

At the present time no effective method has been developed to assure the absence of HBV infectivity from injectable biologics made from pooled plasma, despite testing of donor plasma for hepatitis B surface antigen (HBsAg). Derivatives which are too labile to withstand heating, such as Antihemophilic Factor (Factor VIII, AHF) and Factor IX Complex (Factor IX) may transmit HBV infections despite the absence of detectable HBsAg. In the present development, there is noted a new experimental method for utilizing hepatitis B immune globulin to remove HBV infectivity from labile injectable biologic products.

The ability of this high titer antibody to HBsAg (anti-HBs) to neutralize the infectivity of HBV in such products offers the potential to prevent many cases of hepatitis B in several high risk populations which rely on the receipt of such derivatives to stay alive as well as cases related to therapeutic use of such products in infants and adults not congenitally deficient with regard to the materials contained in such products. Heat-labile products, such as AHF and Factor IX, are made from large pools of plasma from many donors and have a statistical risk of containing a unit with HBV but below the level of detectability for HBsAg. Such plasma derivatives are administered to thousands of hemophiliac patients each year. Greater than 20% of adult hemophiliacs have a history of having had clinically recognized hepatitis, and 60–90% can be shown by serologic tests to have had hepatitis B. Newly diagnosed patients with hemophilia who receive AHF or Factor IX for the first time are at a particularly high risk for acquiring HBV infection as are non-hemophiliac infants and adults who receive these products.

PRIOR ART STATEMENT

U.S. Pat. No. 4,087,519 Trepo—The utilization of gamma globulin fractions to compete and neutralize antigen-e, better described at column 7.

Tabor et al, "A New Use for High Titer Immunoglobulin for the Prevention of Hepatitis B," Hepatitis Scientific Memoranda, November 1979.

Tabor et al, "A New Use for High Titer Immunoglobulins for the Prevention of Hepatitis B," presented at Workshop on Immunoglobulins, October 1979.

DOSAGE

The dose of hepatitis B immune globulin used in this application and development was 5 ml. The 5 ml value is calculated on an average adult and itself is calculated on the basis of 0.06 ml/kg of body weight. Thus, a preferred dosage for hepatitis B immune globulin is a titer of 1 to 100,000 utilizing 5 ml. Realizing the limited supply and high cost of the preparation, it may be possible in the future in specific cases to lower the dosage of hepatitis B immune globulin and in this way permit lower cost and greater availability of the material used.

EXAMPLE 1

A lot of Factor IX made by a United States manufacturer was reconstituted and vialed in 30 ml aliquots. To each vial $10^{3.5}$ chimpanzee infectious doses ($CID_{50}$) from a well documented infectious human serum inoculum (HBsAg subtype adw) were added and incubated for one hour at 37° C. To two "treated" vials, 5 ml of hepatitis B immune globulin from a single lot released by the Bureau of Biologics were added. All three vials, two treated and one untreated, were then incubated for one additional hour at 37° C.

Each vial was inoculated intravenously into a colony born chimpanzee (#918, #960, #961) age 27–36 months, and weighing 11–13 kg, which had never been inoculated with hepatitis B virus (HBV) and had no serologic markers of HBV. The dose of Factor IX administered was similar to that used clinically, approximately 50 U/kg of body weight; the average dose of hepatitis B immune globulin was high for these chimpanzees, 0.42 ml/kg of body weight. No clinical side effects were detected during or after administration. Weekly serum samples were obtained from each chimpanzee and tested for aspartate and alanine aminotransferases (AST, ALT) by a spectrophotometer (normal $\leqq$40 IU/l), HBsAg by radioimmunoassay (RIA), antibody to HBsAg (anti-HBs) by RIA, and antibody to hepatitis B core antigen (anti-HBc) by RIA. Chimpanzee #961, which received the untreated Factor IX, developed hepatitis B indicated by detectable HBsAg from weeks 10 through 28. Anti-HBc was first detected at week 15 and remained detectable. AST and/or ALT was elevated from weeks 13 through 40, with peak AST 1325 IU/l (week 29) and peak ALT 595 IU/l (week 30). The two chimpanzees which received the treated Factor IX (#918, #960) did not develop elevations of AST or ALT and did not develop detectable HBsAg. Passively transferred anti-HBc declined from weeks 1–4 and 1–7, respectively, and was not detected at any time thereafter. Passively transferred anti-HBs remained detectable from weeks 1–15. Weekly evaluation of these chimpanzees continued for 52 weeks, during which time neither of the chimpanzees developed hepatitis B.

EXAMPLE 2

A four-year-old child was diagnosed as having hemophilia A following a playground accident. The child had not been previously hospitalized and had never received injections of blood or blood products. Testing of the child's blood revealed no evidence of past or active hepatitis B infection. During the first 24 hours of hospitalization, the child's bleeding was felt to require the administration of 750 U of Antihemophilic Factor VIII Concentrate, a pooled plasma derivative with a high risk of transmitting hepatitis B. Using the method of "immune inactivation" described here, 5 ml of hepatitis B immune globulin was incubated with the Factor VIII concentrate prior to injection into this child. No evidence of hepatitis B was detected in this child during one year of follow up.

For purposes of this specification, the expression hepatitis B immune globulin means the same as high titer anti-HBs immune globulin and refers to immunoglobulin containing anti-HBs in a titer ranging from 1:100 to 1:100,000.

We claim:

1. A method of preventing the transmission of hepatitis B by injectable biological products made from pooled plasma comprising treatment of the biological products with an effective amount of hepatitis B immune globulin in vitro prior to administration to laboratory animals and humans.

2. The method according to claim 1 wherein the hepatitis B immune globulin is added to an original plasma increment or pool.

3. The method according to claim 1 wherein the hepatitis B immune globulin is added to a fraction derived from plasma.

4. The method according to claim 1 wherein the hepatitis B immune globulin is utilized in 5 ml and in a titer of 1-100 to 1-100,000.

5. The method according to claim 1 wherein the hepatitis B immune globulin is added to the final product.

* * * * *